United States Patent [19]

Keith et al.

[11] 4,238,622

[45] Dec. 9, 1980

[54] D,L-2-AMINO-4-(2-AMINOETHOXY)-TRANS-BUT-3-ENOIC ACID DERIVATIVES

[75] Inventors: Dennis D. Keith, Montclair; Manfred Weigele, North Caldwell, both of N.J.

[73] Assignee: Hoffmann-La Roche Inc., Nutley, N.J.

[21] Appl. No.: 824,371

[22] Filed: Aug. 15, 1977

[51] Int. Cl.³ .......................................... C07C 101/28
[52] U.S. Cl. ...................................... 560/39; 560/159; 560/160; 560/169; 560/170; 562/448; 562/564; 260/326 N; 260/456 A
[58] Field of Search ............. 260/534 M; 560/42, 159, 560/170, 169, 137, 39; 562/564, 448

[56] References Cited

U.S. PATENT DOCUMENTS

| | | | |
|---|---|---|---|
| 3,751,459 | 8/1973 | Berger et al. | 260/534 M |
| 3,865,694 | 2/1975 | Berger et al. | 562/564 |
| 3,887,615 | 6/1975 | Keith et al. | 562/564 |
| 3,991,077 | 11/1976 | Uzuki et al. | 260/534 M |
| 4,014,898 | 3/1977 | Keith et al. | 260/293.88 |
| 4,115,105 | 9/1978 | Scannell | 562/564 |

*Primary Examiner*—Natalie Trousof
*Assistant Examiner*—L. Hendriksen
*Attorney, Agent, or Firm*—Jon S. Saxe; Bernard S. Leon; James H. Callwood

[57] ABSTRACT

The amino acid 2-amino-4-(2-aminoethoxy)-trans-but-3-enoic acid can be conveniently prepared via novel intermediates from a 2,2'-disubstituted diethyl ether and a dialkyl N-protected amidomalonate starting material using a multi-step process. Preferred starting materials are bis-2-chloroethyl ether and diethyl acetamidomalonate. The process, in a preferred embodiment, proceeds through the key intermediate ethyl-2-acetamido-4-[2-(2-phthalimido)ethoxy]-but-2-enoate.

4 Claims, No Drawings

D,L-2-AMINO-4-(2-AMINOETHOXY)-TRANS-BUT-3-ENOIC ACID DERIVATIVES

BACKGROUND OF THE INVENTION

It is known in the art that the double bond in methyl 4-methoxybutenoates is stabilized more effectively by the methoxy group than by the ester. See, for example, Rhoads et al., J. Org. Chem., 35, 3352 (1970) and Hine et al., J. Org. Chem., 32, 2600 (1967).

Preparation of dehydroamino acids by elimination of HCl from an N-chloroamide is described by Poisel and Schmidt, Chem. Ber., 108, 2547 (1975).

U.S. Pat. No. 3,865,694 describes a fermentation process for preparing L-2-amino-4-(2-aminoethoxy)-trans-but-3-enoic acid. This material is also described by Pruess et al., J. Antibiot., 27, 229 (1974).

U.S. Pat. No. 4,014,898 describes the synthesis of compounds of the formula

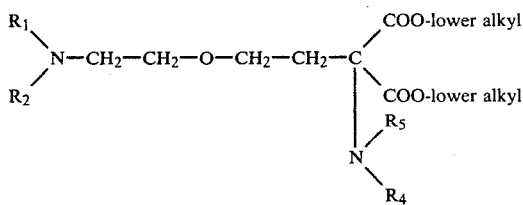

where $R_1$ and $R_2$ are lower alkyl; and $R_4$ and $R_5$, taken together with their attached nitrogen atom form the phthalimido group.

Similarly, U.S. Pat. No. 3,887,615 describes racemic and optically active compounds of the formula

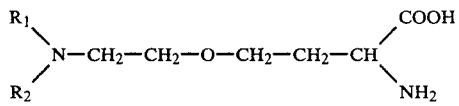

where $R_1$ and $R_2$, each independently, represent hydrogen or lower alkyl, or $R_1$ and $R_2$, taken together with their attached nitrogen atom form a 5- or 6-membered saturated heterocyclic ring wherein said 6-membered ring may contain an additional nitrogen atom or an oxygen atom; provided that one of $R_1$ or $R_2$ is other than hydrogen.

DESCRIPTION OF THE INVENTION

The present invention relates to a process for the preparation of D,L-2-amino-4-(2-aminoethoxy)-trans-but-3-enoic acid. The L-antipode of this compound is a naturally occurring α-amino acid and has been found to inhibit the production of ethylene in plant tissue. The racemic form of the compound also exhibits this utility.

Key intermediates in the present process are compounds of the formula

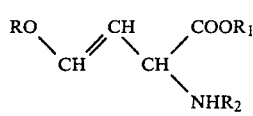

wherein R is 2-phthalimidoethyl, $R_1$ is lower alkyl or aralkyl and $R_2$ is alkanoyl, aroyl, alkoxycarbonyl or aralkoxycarbonyl.

Compounds of formula I are readily prepared by means of a multi-step process starting with a 2,2'-disubstituted diethyl ether of the formula

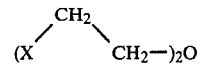

where X is halogen, alkyl sulfonate or arylsulfonate and a N-protected dialkyl amidomalonate of the formula

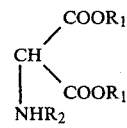

where $R_1$ and $R_2$ are as above.

In the first step of the instant process, an alkali metal salt, preferably a sodium salt formed from Compound III is alkylated with a compound of formula II to yield a 2-substituted ethyl ether of the formula

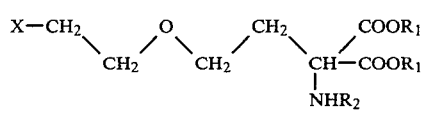

where X, $R_1$ and $R_2$ are as above.

The aforesaid alkylation reaction is conveniently carried out in an inert polar organic solvent such as N,N-dimethylformamide, dimethoxyethane, dimethylsulfoxide and the like at an elevated temperature in the range of about 40° to 150° C. using an excess of compound II. Additionally, the reaction mixture may contain a catalytic amount of an alkali metal iodide, preferably sodium iodide.

Compound IV, prepared above is then reacted with alkali metal phthalimide, preferably potassium phthalimide to give a compound of the formula

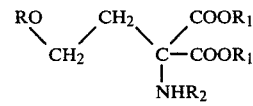

where R, $R_1$ and $R_2$ are as above.

The above reaction is carried out in an inert polar organic solvent such as N,N-dimethylformamide at an elevated temperature in the range of about 50° to 150° C.

In turn, Compound V was de-alkoxycarbonylated utilizing a procedure analogous to that of Krapcho and Lovey, Tetraheydron Lett., 957 (1973) and Krapcho et al., ibid. 1091 (1974) involving reaction at an elevated temperature, i.e., 100°–180° C. in the presence of sodium chloride, water and dimethylsulfoxide to thereby produce a compound of the formula

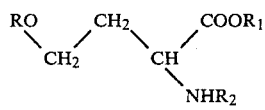

where R, $R_1$ and $R_2$ are as above.

Treatment of a compound of formula VI with a hypochlorite or hypobromite such as t-lower alkyl hypochlorite or hypobromite, i.e., t-butyl hypochlorite or alternatively with a N-halosuccinimide such as N-chlorosuccinimide, N-bromosuccinimide or N-iodosuccinimide in a manner known per se yields compounds of the formula:

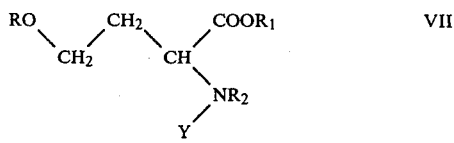   VII where R, $R_1$ and $R_2$ are as above, and Y is halogen selected from chloro, bromo and iodo.

In a preferred method of preparing compounds of formula VII, a compound of formula VI is treated with t-butyl hypochlorite in methanol solution in the presence of an alkaline buffer for example a borax (sodium tetraborate) buffer.

Elimination of HY from a compond of formula VII and isomerization of the resultant acyl imine produces a compound of the formula:

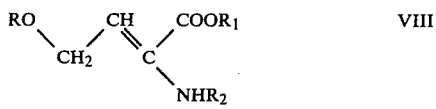   VIII where R, $R_1$ and $R_2$ are as above.

The aforesaid reaction is readily carried out using a tertiary amine base such as 1,4-diazabicyclo[2.2.2]octane (DABCO) in an inert organic solvent such as a halogenated hydrocarbon, preferably carbon tetrachloride, at room temperature.

Deconjugation of the double bond in the compound of formula VIII to form the desired enol ether of formula I is accomplished by heating a solution of the former compound in 1:1 (v/v) triethylamine/pyridine at about 100° C. for periods in the range of from 20 to 60 hours. Fractional crystallization of the resulting solid obtained upon solvent removal yielded the desired compound.

Additional product can be obtained by recycling mother liquors containing the starting material through the triethylamine/pyridine treatment. Moreover, by-product cis isomer enol compound can be equilibrated to a mixture of the trans and cis isomers by treatment with iodine in glyme solution. The trans isomer so produced can be isolated by use of preparative high pressure liquid chromatography and fractional crystallization in a manner known per se.

The conversion of compounds of formula I to the desired D,L-2-amino-4-(2-aminoethoxy)-trans-but-3-enoic acid involves removal of the three protective groups which can be accomplished in a manner known per se. In a preferred embodiment, this is accomplished in a stepwise manner involving first removing the phthalimido group, secondly saponifying the ester and finally removing the $N^\alpha$-protecting group.

Thus, treatment of a compound of formula I with anhydrous hydrazine in lower alkanol solution, i.e., methanol, results in removal of the phthalimido group to yield a compound of the formula

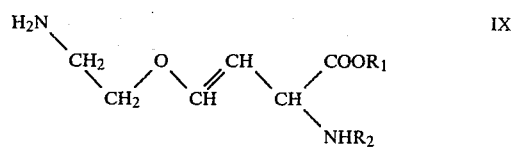   IX where $R_1$ and $R_2$ are as above.

Saponification can be accomplished by conventional procedures known in the art such as by reacting the compound of formula IX with aqueous base such as 1 N potassium hydroxide at an elevated temperature, i.e., in the range between 50° and 100° C. for a period of 12 to 36 hours. There is thus produced after workup and acidification a compound of the formula

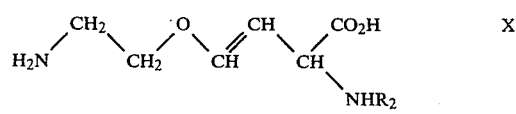   X where $R_2$ is as above.

In the final step the $N^\alpha$-protecting group is removed using procedures known in amino acid chemistry for this purpose. The procedure selected will, of course, depend on the nature of the protective group present. For example, a suitable procedure for removing an N-acetyl group involves treatment with hydrazine hydrate at elevated temperatures in the range of 50° to 100° C. for 12 to 72 hours.

Additional product can be obtained by recycling the mother liquors from the final reaction after isolation of product through the base hydrolysis step. It is believed that such liquors contain a compound of the formula:

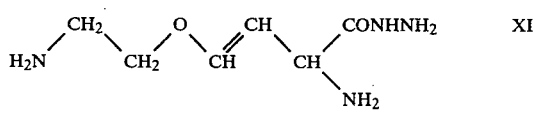   XI which most likely arises by hydrazinolysis of the ester compound IX during removal of the phthalimide group.

The racemic product obtained from the aforesaid synthesis can be resolved, if desired, into the natural L-antipode by resolution procedures well known in the art for resolving amino acids. A suitable procedure involves, for example, forming a diastereomeric salt with optically active acids or bases, fractionally crystallizing the salts, and then decomposing the desired diastereomeric salt to yield the desired L-2-amino-4-(2-aminoethoxy)-trans-but-3-enoic acid.

As used herein, the term "lower alkyl" means a straight-chain or branched-chain alkyl group which preferably contains from 1 to 6 carbon atoms such as methyl, ethyl, propyl, tert-butyl and the like. A preferred alkyl sulfonate is methyl sulfonate (mesyl) while a preferred aryl sulfonate is tolyl sulfonate (tosyl). Examples of aralkyl groups include benzyl and phenethyl. Suitable alkanoyl groups include acetyl, propionyl, hexanoyl, and the like. The term "aroyl" preferably means benzoyl. An example of an alkoxycarbonyl group is tert-butoxycarbonyl while benzyloxycarbonyl is a preferred aralkoxycarbonyl.

It should be noted that a large number of protective groups are known in amino acid chemistry for the protection of carboxy and amino groups during synthesis.

Such groups may be utilized as equivalents for the specifically disclosed moieties above.

The present invention is further illustrated by the following Examples.

EXAMPLE 1

Ethyl-2-acetamido-4-(2-chloroethoxy)-2-ethoxycarbonylbutyrate

Sodium hydride (30.9 g. of 50% oil dispersion; 0.65 mol) was placed in a dry 3-neck flask equipped with a mechanical stirrer, an addition funnel, a reflux condenser and an argon inlet. The hydride was washed with hexane and dried under a stream of argon. Dry N,N-dimethylformamide (500 ml.) was added and the suspension cooled to 5° in an ice bath. Diethylacetamidomalonate (140 g.; 0.65 mol.) was added in portions with stirring at a rate which maintained a vigorous effervescence. After the addition was complete and the effervescence subsided, sodium iodide (9.66 g.; 0.065 mol.) was added in one portion and 460 g. (3.2 mol.) of bis-2-chloroethyl ether was added rapidly through the addition funnel. The reaction mixture was then heated at 60° with stirring for 24 hours. The mixture was transferred to a one-neck flask and concentrated in vacuo on a rotary evaporator (600-800 ml. removed). The residue was subjected to steam distillation until the distillate was clear (2-2.5 L). The pot residue was taken up in 500 ml. of ether and the organic solution washed 5 times with 100 ml. portions of brine. The ether solution was dried over anhydrous sodium sulfate and concentrated in vacuo to yield 175.7 g. (84.5%) of crude product. This material is suitable for use in the next step.

A portion was purified by distillation to yield pure product: bp 135°–140°/0.1 mm; ir (CHCl$_3$) 3400, 1715, 1655, 1470 cm$^{-1}$; NMR (CDCl$_3$) δ6.96 (broad, 1H, NH), 4.22 (q, 4H, J=6 Hz, 2 CH$_3$CH$_2$O—), 3.5 (m, 6H, ClCH$_2$CH$_2$OCH$_2$—), 2.65

(t, 2H, J = 6 Hz, —CH$_2$CH$_2$C$\lessgtr$), 2.03 (s, 3H, CH$_3$CO—), 1.25 (t, 3H, J=6 Hz, CH$_3$CH$_2$O—); mass spectrum m/e 324 (M$^+$ +H), 217, 93, 63.

Anal. Calcd. for C$_{13}$H$_{22}$ClNO$_6$: C, 48.23; H, 6.85; N, 4.33. Found: C, 48.06; H, 6.71; N, 4.18.

EXAMPLE 2

Ethyl 2-acetamido-2-ethoxycarbonyl-4-[2-(2-phthalimido)ethoxy]-butyrate

A 3-neck flask equipped with a mechanical stirrer, a reflux condenser, and an argon inlet was charged with 128.1 g. (0.396 mol) of the chloro acetamidomalonate of Example 1, 109.9 g. (0.59 mol.) potassium phthalimide, 6.57 g. (0.04 mol.) potassium iodide and 600 ml. of dry N,N-dimethylformamide. The mixture was heated with stirring under argon at 100° for 18 hours. The reaction mixture was allowed to cool and divided into two equal portions which were processed as follows: each was diluted with 2 L of ether causing salts to precipitate. The solids were removed by filtration through diatomaceous earth and the filtrates concentrated in vacuo to remove the ether and N,N-dimethylformamide. The residues were each diluted with 1.5 L of ether and 100 ml. of ethyl acetate. The organic phases were washed six times with water (300 ml.) and once with brine (300 ml.). The organic solutions were combined, dried with anhydrous sodium sulfate and concentrated in vacuo until crystallization began. At that point, the mixture was heated on the steam bath until a clear solution was obtained. The solution was diluted with hexane until the cloud point and then set aside to crystallize. Pure product was collected in two crops (111.6 g.; 65%): mp 101°–103°; uv (EtOH) max 220 nm (ε42,200), infl 240 (4300), 293 (920); ir (CHCl$_3$) 3410, 1775, 1738, 1712, 1678, 1495 cm$^{-1}$; NMR (CDCl$_3$) δ8.0 (broad, 1H, NH), 7.88 (s, 4H, aromatic), 4.13 (q, 4H, J=7 Hz, CH$_3$CH$_2$O—), 3.5 (m, 6H, PhthNCH$_2$CH$_2$OCH$_2$—), 2.45

(t, 2H, J = 6 Hz, —OCH$_2$CH$_2$C$\lessgtr$), 2.03 (s, 3H, CH$_3$CO), 1.15 (t, 3H, J=7 Hz, CH$_3$CH$_2$O—); mass spectrum m/e 389, 361, 319, 244, 217.

Anal. Calcd. for C$_{21}$H$_{26}$N$_2$O$_8$: C, 58.06; H, 6.03; N, 6.45. Found: C, 58.32; H, 5.79; N, 6.40.

EXAMPLE 3

Ethyl 2-acetamido-4-(2-(2-phthalimido)ethoxy]butyrate

A suspension consisting of 143.6 g. (0.331 mol) phthalimido acetamidomalonate of Example 2, 11.9 g. (0.66 mol.) water, 19.3 g. (0.33 mol.) sodium chloride, and 330 ml. of dimethyl sulfoxide was heated with magnetic stirring at 170° under argon for 8 hours. The reaction mixture was allowed to cool to room temperature, diluted with 1500 ml. ethyl acetate and washed two times with 350 ml. portions of water, followed by six 100 ml. water washes and two 300 ml. brine washes. Each aqueous layer was backwashed with a small portion of ethyl acetate which was then added to the main organic phase. The ethyl acetate solution was dried over anhydrous sodium sulfate and concentrated in vacuo to yield 91.7 g. (77%) of product as a brown oil. This material was suitable for use in the next step.

An analytical sample was prepared by taking a portion of the oil in ether, treating the solution with charcoal and filtering through diatomaceous earth. The filtrate was concentrated in vacuo and the filtrate crystallized from ethyl acetate/petroleum ether to yield pure product: mp 90°–90.5°; uv (EtOH) max 219 nm (ε40,600), infl 232 (13,400), 240 (9400), 294 (1900), infl 300 (1800); ir (CHCl$_3$) 3300, 1775, 1730, 1720, 1640, 1555 cm$^{-1}$; NMR (CDCl$_3$) δ7.8 (m, 4H, aromatic H), 6.73 (broad, 1H, NH), 4.64 (m, 1H, —CH$_2$CH<), 4.08 (q, 2H, J=8 Hz, CH$_3$CH$_2$O—), 3.9–3.4 (m, 6H, PhthNCH$_2$CH$_2$OCH$_2$—), 2.07 (s, 3H, CH$_3$CO-), 2.02 (t, 2H, J=6 Hz, —OCH$_2$CH$_2$CH<), 1.17 (t, 3H, J=8 Hz, CH$_3$CH$_2$O-); mass spectrum m/e 362 (M$^+$), 317, 289, 160.

Anal. Calcd. for C$_{18}$H$_{22}$N$_2$O$_6$: C, 59.66; H, 6.12; N, 7.73. Found: C, 59.80; H, 6.32; N, 7.75.

EXAMPLE 4

Ethyl 2-(N-chloroacetamido)-4-[2-(2-phthalimido)ethoxy]butyrate

A solution consisting of 73.8 g. (0.204 mol.) of acetamide from Example 3, 8.69 g. (0.023 mol.) sodium tetraborate, and 224 ml. of methanol was protected from light and cooled with an ice bath to 5° under an atmosphere of argon. t-Butyl hypochlorite (37.1 ml, 0.31 mol.) was added with magnetic stirring to the solution. The ice bath was removed after addition was complete. After 45 minutes an alliquot was removed and tlc analysis [silica gel plates; CHCl$_3$/Et$_2$O (8:1)] showed that some starting material was still present. More t-butylhypochlorite was added in portions until tlc analysis indicated that the reaction was complete. The reaction solution was then concentrated in vacuo with protection from light yielding an oil which was taken up in carbon tetrachloride (350 ml.), causing sodium salts to precipitate. The solids were removed by filtration yielding a carbon tetrachloride solution of product which was used directly in the next step.

EXAMPLE 5

Ethyl 2-acetamido-4-[2-(2-phthalimido)ethoxy]but-2-enoate

To the carbon tetrachloride solution of the Example 4 product was added 25.2 g. (0.224 mol.) of 2,4-diazabicyclo[2.2.2]octane (DABCO). The resultant solution was stirred magnetically for 15 hours. A copious white precipitate formed after 2 hours.

Ethyl acetate (1L) was added to the mixture to break up the precipitate. After allowing time for the solid to settle, the solution was decanted, and the remaining precipitate washed twice with 500 ml. portions of ethyl acetate. The combined organic solutions were filtered through diatomaceous earth and the filtrate concentrated in vacuo. The residue was taken up in chloroform and passed through a column (id 47 mm) of silica gel 60 (100 g.) packed in chloroform. The column was developed with 2 L of chloroform and the chloroform solution concentrated in vacuo to yield an oil. Crystallization from ethyl acetate/ether/hexane yielded in two crops 68.1 g. (92.9%) of butenoate product, mp 113°–116°. The average yield of product obtained from several large scale preparations was 81%. An analytical sample was prepared by recrystallization from the same solvent: mp 120°–122.5°; uv (EtOH) max 220 ($\epsilon$49,200), infl 233 (21,000), infl 241 (15,700), 294 (1930), infl 300 (1800); ir (CHCl$_3$) 3410, 1775, 1713, infl 1695, 1495 cm$^{-1}$; NMR (CDCl$_3$) $\delta$7.80 (m, 4H, aromatic H), 7.53 (broad, 1H, NH), 6.51 (t, 1H, J=6 Hz, —OCH$_2$CH=), 4.24 (q, 2H, J=8 Hz, CH$_3$CH$_2$O—), 4.18 (d, 2H, J=6 Hz, —OCH$_2$CH=), 3.93 and 3.74 (2 m, 2H in each, —NCH$_2$CH$_2$O—), 2.13 (s, 3H, CH$_3$CO—), 1.29 (t, 3H, J=8 Hz, CH$_3$CH$_2$O); mass spectrum m/e 360 (M+), 317, 314, 287, 174, 160.

Anal. Calcd. for C$_{18}$H$_{20}$N$_2$O$_6$: C, 59.99; H, 5.59; N, 7.77. Found: C, 60.20; H, 5.56; N, 7.80.

EXAMPLE 6

Ethyl 2-acetamido-4-[2-(2-phthalimido)ethoxy]-trans-but-3-enoate (A) and ethyl 2-acetamido-4-[2-(2-phthalimido)ethoxy]-cis-but-3-enoate (B)

A solution consisting of 74.5 g. (0.21 mol.) of butenoate from Example 5, 487 ml of triethylamine and 485 ml. of pyridine was heated with stirring at reflux temperature under an atmosphere of argon for 37 hours. The solution was allowed to cool and concentrated in vacuo. Ethyl acetate was added to the remaining oil and the solution concentrated again in vacuo. After repeating this process one more time, the dark brown residue was dissolved in ethyl acetate and the resultant solution was brought to the cloud point with hexane and set aside overnight to crystallize. The resultant light brown solid was collected and was shown by NMR to consist mainly of the trans and cis enol ethers (A) and (B). The filtrate from this crystallization was concentrated in vacuo yielding a dark oil which was processed as described below.

The solid was dissolved in a minimum amount of ethyl acetate and the resultant solution applied to a column (id 47 mm) of silica gel 60 (100 g.) packed in ethyl acetate. The column was developed with ethyl acetate until all uv absorbing material was eluted. The ethyl acetate solution was concentrated in vacuo. Ether was added until the cloud point was reached, and the solution allowed to stand undisturbed overnight while crystallization occurred (occasionally scratching or seed crystals were used to induce crystallization). The crystals which were deposited were collected by filtration (30.2 g., 41%) and were shown by NMR to be approximately an 85:15 mixture of trans and cis enol ethers. A further crystallization from the same solvent system gave 25.5 g. (34%) of (A): mp 95°–96.5°; uv (EtOH) max 219 nm ($\epsilon$49,400), 239 (11,200), 293 (2020), infl 300 (1860); ir (CHCl$_3$) 3435, 1778, 1717, 1678, 1504 cm$^{-1}$; NMR (CDCl$_3$) $\delta$7.8 (m, 4H, aromatic H), 6.52 (d, 1H, J=12 Hz, OCH=CH), 6.25 (broad, 1H, NH), 4.6–5.0 (m, 2H, —OCH=CHCH), 4.16 (q, 2H, J=8 Hz, CH$_3$CH$_2$O—), 3.94 (broad s, 4H, NCH$_2$CH$_2$O—), 1.97 (s, 3H, CH$_3$CO—), 1.24 (t, 3H, J=8 Hz, CH$_3$CH$_2$O—); mass spectrum m/e 360 (M+), 317, 314, 287, 174 (base), 160.

Anal. Calcd. for C$_{18}$H$_{20}$N$_2$O$_6$: C, 59.99; H, 5.59; N, 7.77. Found: C, 59.96; H, 5.41; N, 7.65.

The mother liquors from the crystallizations described above contained varying amounts of the starting material, trans enol ether (A) and the cis enol ether (B). Liquors which contained a large amount of starting material were resubjected to the reaction with triethylamine and pyridine. Such material was processed as described above to yield further quantities of trans enol ether (A).

Mixtures consisting principally of the cis enol ether were treated with iodine (20 mg. I$_2$/g mixture) in dry peroxide-free glyme (10 ml/g mixture) at 40° for 40 hours. The reaction mixture was concentrated in vacuo leaving a residue which was dissolved in ethyl acetate. The solution was washed with 10% sodium thiosulfate solution and dried over anhydrous sodium sulfate. Concentration on a rotary evaporator yielded an oil consisting of a 3:2 mixture of trans and cis enol ethers, respectively, as determined from the NMR spectrum. This material was chromatographed in batches of 5 g. each on a Waters Prep LC/System 500 with one PrePAK$^T$-$M$-500/Silica Cartridge using ethyl acetate/hexane/methanol (10:10:1) as the eluent. Several recycles were required for complete separation of the isomers. The $\alpha,\beta$-unsaturated ester starting material was eluted first, followed by the trans enol ether (A), and then the cis enol ether (B). Concentration of the appropriate fractions followed by crystallization yielded approximately 1 g. of pure (A) for each 5 g. of 3:2 mixture.

By diligently following these procedures, yields between 50 and 65% were realized for the trans enol ether (A). Concentration of the fractions containing the cis isomer, followed by crystallization from ethyl acetate/petroleum ether gave (B): mp 88°–90°; uv (EtOH) max 218 nm (ε42,800), infl 239 (9800), 292 (1870), infl 300 l (1750); ir (CHCl$_3$) 3435, 3410, 1775, 1715, 1670, 1513 cm$^{-1}$; NMR (CDCl$_3$) δ7.8 (m, 4H, aromatic H), 6.65 (broad, 1H, NH), 6.07 (d, 1H, J=6 Hz, —OCH=CH—), 5.07 (t, 1H, J=8 Hz, —OCH=CHCH<), 4.61 (dd, 1H, J=6 and 8 Hz, —OCH=CH—), 4.0 (m, 6H, CH$_3$CH$_2$O— and >NCH$_2$CH$_2$O—), 2.06 (s, 3H, CH$_3$CO—), 1.17 (t, 3H, J=7 Hz, CH$_3$CH$_2$O—); mass spectrum m/e 360 (M+), 317, 314, 287, 174 (base), 160, 147, 130.

Anal. Calcd. for C$_{18}$H$_{20}$N$_2$O$_6$: C, 59.99; H, 5.59; N, 7.77. Found: C, 59.86; H, 5.41; N, 7.65.

EXAMPLE 7

D,L-2-amino-4-(2-aminoethoxy)-trans-but-3-enoic acid

The protecting groups were removed from the trans product of Example 6 by the following multi-step procedure: a solution consisting of 3.5 g. (0.0097 mol.) of enol ether (A), 0.47 g. (0.0146 mol.) anhydrous hydrazine, 10 ml. of methanol, and 17 ml. of ethanol was stirred magnetically under argon for 24 hours. During this time, a copious white precipitate formed which stopped the stirring. The solid is most probably the salt which results from the reaction of the freed epsilon amine with the newly formed phthalhydrazide.

At this point, 60 ml. of 1 N KOH was added directly to the reaction flask containing ethyl 2-acetamido-4-(2-aminoethoxy)-trans-but-3-enoate causing the solid to dissolve. The resultant solution was heated at 90° under argon for 24 hours. The reaction mixture was allowed to cool to ambient temperature, concentrated in vacuo to approximately ½ its original volume, and acidified with 1 N HCl (3 N HCl in larger scale runs) to pH 4. This caused the precipitation of phthalhydrazide which was removed by filtration. The pH of the filtrate, which contains D,L-2-acetamido-4-(2-aminoethoxy)-trans-but-3-enoic acid was adjusted to between 6 and 7 and the filtrate then concentrated in vacuo. The residue was dissolved in 25 ml. of 85% hydrazine hydrate and the solution heated at 80° for 40 hours. After cooling to ambient temperature, the reaction mixture was concentrated in vacuo to remove the hydrazine hydrate. The residue was dissolved in water and the pH of the solution adjusted to between 9 and 10. The solution was concentrated in vacuo giving a yellow solid which was dried in vacuo over P$_2$O$_5$ for 4 hours and then over conc. H$_2$SO$_4$ (16 hours).

The resultant yellow residue was taken up in water and applied to a cation exchange column (10 fold excess of AG$^R$ 50W-X4; 100–200 mesh; H$^+$ form). The column was washed with water and 10% aqueous pyridine. The amino acid product was eluted with 1.5 N NH$_4$OH. The fraction was concentrated in vacuo and the residue dried for a short time at 0.1 mm. It was then dissolved in water and the pH of the solution adjusted to 3.6 with 1 N HCl. Concentration of the solution, followed by crystallization of the resultant oil from water/methanol gave 0.658 g. (35%) of the monohydrochloride salt of the product. An analytical sample was prepared by recrystallization: mp 187.5°–189° (dec); ir (KBr) 3500–2250 (broad), 1650, 1600, 1500; NMR (D$_2$O) δ7.35 (d, 1H, J=12.4 Hz, —OCH=CH—), 5.53 (dd, 1H, J=10 and 12.4 Hz, —OCH=CHCH<), 4.71 (d, 1H, J=10 Hz, —OCH=CHCH<), 4.58 (m, 2H, —OCH$_2$CH$_2$N<), 3.85 (m, 2H, —OCH$_2$CH$_2$N<).

Anal. Calcd. for C$_6$H$_{12}$N$_2$O$_3$.HCl: C, 36.65; H, 6.66; N, 14.25. Found: C, 36.44; H, 6.57; N, 14.08.

We claim:

1. A racemic compound of the formula

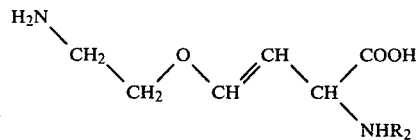

where R$_2$ is protecting group which is alkanoyl, aroyl, alkoxycarbonyl or aralkoxycarbonyl.

2. The compound of claim 1 which is D,L-2-acetamido-4-(2-aminoethoxy)-trans-but-3-enoic acid.

3. A racemic compound of the formula

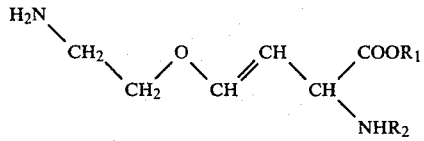

where R$_1$ is lower alkyl or aralkyl and R$_2$ is a protecting group which is alkanoyl, aroyl, alkoxycarbonyl or aralkoxycarbonyl.

4. The compound of claim 3 which is D,L-ethyl 2-acetamido-4-(2-aminoethoxy)trans-but-3-enoate.

* * * * *